United States Patent [19]

Fernschild, deceased, et al.

[11] Patent Number: 5,315,046

[45] Date of Patent: May 24, 1994

[54] PROCESS FOR PREPARING ETHANE DERIVATIVES

[75] Inventors: Guenter Fernschild, deceased, late of Hannover, by Claudia Gerdan, legal representative; Werner Rudolph, Hannover; Carsten Brosch, Seelze, all of Fed. Rep. of Germany

[73] Assignee: Kali-Chemie AG, Hannover, Fed. Rep. of Germany

[21] Appl. No.: 658,658

[22] Filed: Feb. 21, 1991

[30] Foreign Application Priority Data

Feb. 26, 1990 [DE] Fed. Rep. of Germany ....... 4005945

[51] Int. Cl.$^5$ ............................................. C07C 17/08
[52] U.S. Cl. .................................................. 570/167
[58] Field of Search ........................................ 570/167

[56] References Cited

U.S. PATENT DOCUMENTS 2,500,218  3/1950  Towne et al. ...................... 570/167

FOREIGN PATENT DOCUMENTS 609770  11/1960  Canada ............................... 570/167
589167   6/1947  United Kingdom ................ 570/167

*Primary Examiner*—Alan Siegel
*Attorney, Agent, or Firm*—Evenson, McKeown, Edwards & Lenahan

[57] ABSTRACT

A process for preparing ethane derivatives containing the trifluoromethyl group in good yield is described which is carried out in liquid phase and is particularly suitable for preparing $CF_3CHCl_2$ (R123).

15 Claims, 1 Drawing Sheet

PROCESS FOR PREPARING ETHANE DERIVATIVES

BACKGROUND OF THE INVENTION

This invention relates to a process for preparing ethane derivatives containing the trifluoromethyl group corresponding to the formula $CF_3CHYZ$, in which Y and Z may be the same or different and are hydrogen, chlorine or bromine or fluorine.

Perhalogenated organic compounds which are used as refrigerants, degreasing agents, lubricants and release agents or in the production of plastic foams, are increasingly being replaced by hydrogen-containing halogenated organic compounds.

One class of compounds highly suitable as substitutes for perhalogenated organic compounds is that of trifluoromethyl-containing ethane derivatives corresponding to the formula $CF_3CHYZ$ in which Y and Z may be the same or different and are hydrogen, fluorine, chlorine or bromine.

Compounds of this type can be prepared by halogen/fluorine exchange which is usually a chlorine/fluorine exchange. One disadvantage of known preparation processes is the poor yield. Furthermore, undesirable perhalogenated by-products are often also formed.

However, the industrial preparation of these compounds is not without problems. The reason for this is that the more highly halogenated compounds are relatively inert towards chemical reactions.

Processes for preparing $CF_3CHCl_2$ are known. One preparation of $CF_3CHCl_2$ in the liquid phase is described in A. E. Feiring, *J. Fluor. Chem.*, Vol. 13, pp. 7-18 (1979). There, fluorotetrachloroethane is reacted with hydrogen fluoride in the liquid phase in the presence of tantalum pentafluoride catalyst. The yield of $CF_3CHCl_2$ is about 10%. Starting from tetrachloroethylene, the preparation is only possible with one single catalyst, namely again with tantalum pentafluoride, but in a yield of only 2%.

A gas phase process considered the only industrially useful process for preparing $CF_3CHCl_2$ is described European Patent Application No. EP 282,005. The preparation of $CF_3CHCl_2$ is carried out at temperatures of 320° to 360° C. by reacting tetrachloroethylene with hydrogen fluoride on aluminum fluoride/chromium oxide catalysts. The degree of conversion and yield in this process are unsatisfactory, and the energy consumption naturally very high.

SUMMARY OF THE INVENTION

It is the object of the invention to provide an improved process for preparing ethane derivatives corresponding to the formula $CF_3CHYZ$ in liquid phase.

This and other objects are achieved by providing a process for preparing ethane derivatives of the general formula (I)

$$CF_3CHYZ \qquad (I)$$

in which Y and Z may be the same or different and Y is hydrogen, fluorine, chlorine or bromine and Z is hydrogen, fluorine, chlorine or bromine, comprising:
reacting at least one ethane derivative corresponding to the formula II:

$$CHal^1Hal^2Hal^3CHYZ \qquad (II)$$

in which Y and Z have the above meanings, $Hal^1$ is halogen, $Hal^2$ is halogen and $Hal^3$ is halogen with the exception of fluorine with essentially anhydrous hydrogen fluoride in liquid phase in the presence of an essentially anhydrous, catalytically active solution of a hydrogen fluoride addition compound corresponding to the formula III:

$$H_2F^+(SbCl_xF_y)^- \qquad (III)$$

in which x plus y=6, and x=0 to 1 and y=5 to 6, in hydrogen fluoride, and
recovering the resulting ethane derivative of formula (I) from the reaction mixture.

BRIEF DESCRIPTION OF THE DRAWINGS

The invention will be described in further detail with reference to the accompanying drawing which is a schematic illustration of an apparatus for carrying out the process of the invention.

DETAILED DESCRIPTION OF PREFERRED EMBODIMENTS

Figure 1:
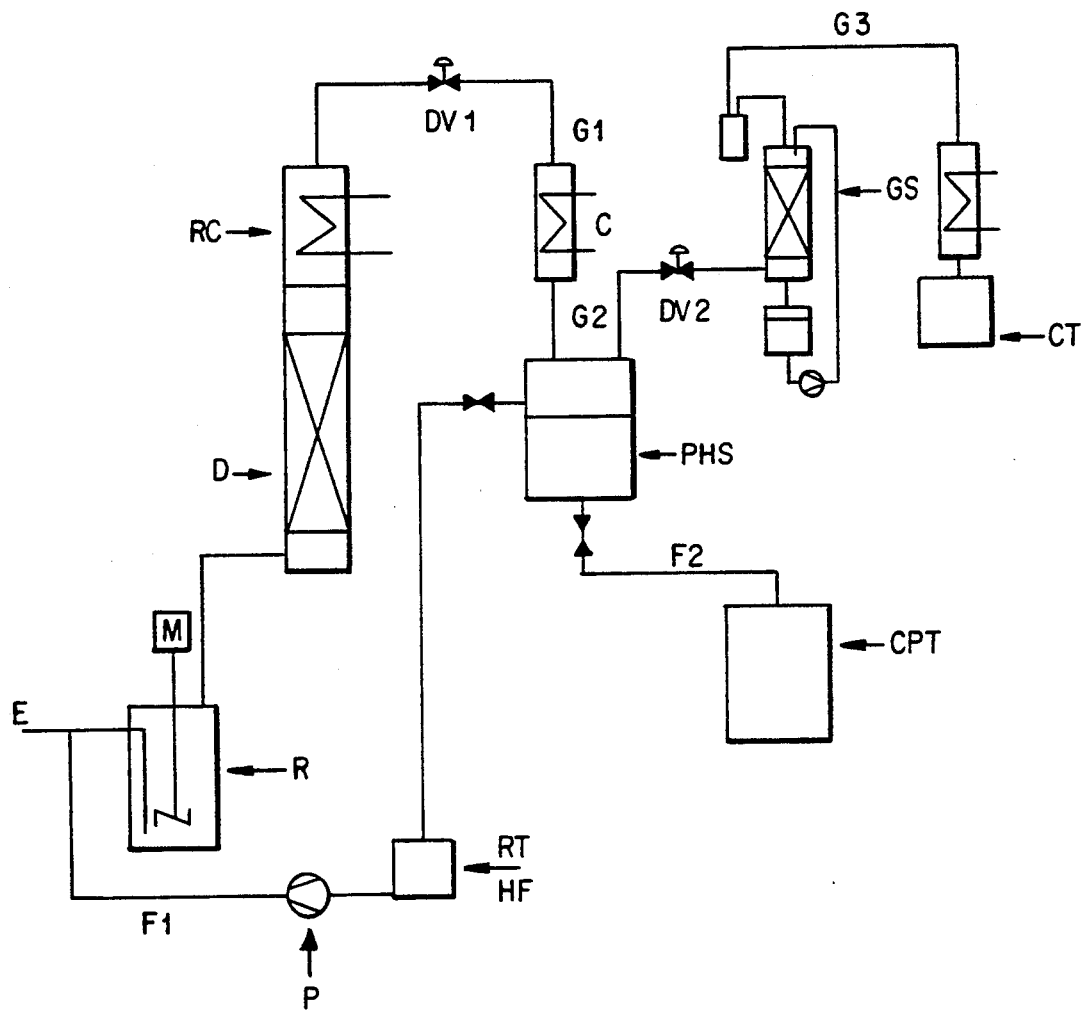

The process according to the invention for preparing ethane derivatives of the general formula (I)

$$CF^3CHYZ \qquad (I)$$

in which Y and Z may be the same or different and Y is hydrogen, fluorine, chlorine or bromine and Z is hydrogen, fluorine, chlorine or bromine, is characterized in that ethane derivatives of the general formula (II)

$$CHal^1Hal^2Hal^3CHYZ \qquad (II)$$

in which Y and Z have the above meanings, $Hal^1$ is halogen, $Hal^2$ is halogen and $Hal^3$ is halogen with the exception of fluorine, or mixtures of ethane derivatives of the general formula (II) are reacted with substantially anhydrous hydrogen fluoride in liquid phase in the presence of a substantially anhydrous, catalytically active solution of a hydrogen fluoride addition compound of the general formula (III)

$$H_2F^+(SbCl_xF_y) \qquad (III)$$

in which x and y add up to 6; x has a value of 0 to 1, and y a value of 5 to 6, in hydrogen fluoride, and the resulting ethane derivative of the general formula (I) is recovered from the reaction mixture.

Compounds of the formula II in which $Hal^3$ is chlorine and $Hal^1$ and $Hal^2$ are fluorine or chlorine are preferably used. Y and Z are preferably cholorine.

In the compounds of formula III, x and y add up to 6. Preferably, x has a value of 0 to 0.5 and y a value of 5.5 to 6. It is especially preferred if x is 0 and y is 6.

The ethane derivatives used as starting compounds are known and can be prepared by known processes. It is also possible to use mixtures.

Suitable compounds of the formula (I) which can be prepared according to the invention include, for example, $CF_3CH_3$, $CF_3CH_2Cl$, $CF_3CH_2Br$, $CF_3CHCl_2$, $CF_3CHBrCl$ and $CF_3CHBr_2$. The process is particularly suitable for preparing $CF_3CH_2Cl$ and $CF_3CHCl_2$, in particular for preparing $CF_3CHCl_2$.

The reaction is started with compounds of the general formula (II), in which the group —CHXY has the same meaning in the compounds of formula (I) and in the compounds of formula (II).

It is, for example, also possible to start with $CBrCl_2CH_2Cl$, $CF_2BrCH_2Cl$ or preferably $CCl_3CH_2Cl$, $CFCl_2CH_2Cl$, $CF_2ClCH_2Cl$ or mixtures of these compounds in order to prepare $CF_3CH_2Cl$.

It is, for example, possible to start with $CBrCl_2CHCl_2$, $CF_2BrCHCl_2$ or preferably $CCl_3CHCl_2$, $CFCl_2CHCl_2$, $CF_2ClCHCl_2$ or mixtures of these compounds in order to prepare $CF_3CHCl_2$.

If desired, the ethane derivative used can be a mixture containing a compound of the formula (IIa)

$$CFHal^2Hal^3CHYZ \qquad (IIa)$$

in which $Hal^2$, $Hal^3$, Y and Z have the above meanings, which mixture is prepared in situ by reacting an ethene compound of the general formula (IV)

$$CHal^2Hal^3=CYZ \qquad (IV)$$

in which $Hal^2$, $Hal^3$, Y and Z have the above meanings, with substantially anhydrous hydrogen fluoride in liquid phase in the presence of the catalytically active solution.

The process according to the invention is carried out using substantially anhydrous hydrogen fluoride. This is understood to mean hydrogen fluoride having a water content of less than 0.1% by weight, preferably a water content of less than 0.01% by weight. When hydrogen fluoride is mentioned hereinafter, it is always understood to mean substantially anhydrous hydrogen fluoride.

Advantageously, the ethane derivative and, if desired, further hydrogen fluoride is introduced into the catalytically active solution.

The invention will now be illustrated in further detail by the preparation of $CF_3CHCl_2$ from $CFCl_2CHCl_2$, $CF_2ClCHCl_2$, $CCl_3CHCl_2$ or mixtures of these compounds.

The preparation of the catalytically active solution will be described next.

It is known that pentavalent antimony pentafluoride is in equilibrium in liquid hydrogen fluoride with $H_2F^+(SbF_6)^-$ $$2HF + SbF_5 \leftrightarrow H_2F^+(SbF_6)^-$$

Such an equilibrium not only exists between hydrogen fluoride and antimony pentafluoride, but also between hydrogen fluoride and $SbCl_nF_{5-n'}$, in which n' has a value from 0 to 1:

$$2HF + SbCl_nF_{5-n'} \leftrightarrow H_2F^+(SbCl_xF_y)^-$$

The equilibrium can be shifted toward the hydrogen fluoride addition compound by adding excess hydrogen fluoride.

Thus, the catalytically active solution is advantageously produced by reacting an antimony compound of the formula $SbCl_nF_{5-n}$, in which n has a value from 0 to 5, with an amount of hydrogen fluoride sufficient to form a solution of the compound of the formula III in hydrogen fluoride at such a temperature and such a pressure that the $SbCl_nF_{5-n}$ is substantially completely reacted to form $H_2F^+(SbCl_xF_y)^-$, in which x and y have the aforementioned meanings.

This can be achieved by various methods. A catalytically active solution can be produced in a particularly simple manner by reacting antimony pentafluoride with hydrogen fluoride. Advantageously, at least 2 moles of hydrogen fluoride are used per mole of antimony pentafluoride. In this case, the catalytically active solution is already formed at room temperature. Advantageously, the reaction is carried out at elevated pressure in order to maintain the hydrogen fluoride in a liquid phase.

The catalytically active solution can also be prepared by reacting antimony pentahalide, for example pentavalent antimony chloride-fluoride or, preferably, antimony pentachloride with hydrogen fluoride at elevated temperature and elevated pressure. When using antimony pentachloride, the reaction is preferably carried out at temperatures between about 20° C. and 100° C. and pressures of 0.5 to 8 bar (abs). The course of the reaction can be monitored, for example, by means of the resulting hydrogen chloride which forms. The reaction can be stopped as soon as at least 4 moles, preferably at least 4.5 moles, or more hydrogen chloride have been liberated per mole of antimony pentachloride used.

In the context of the present invention, it is important that the antimony pentahalide present is predominantly in the form of the hydrogen fluoride addition compound of the general formula $H_2F^+(SbCl_xF_y)$, in which x and y add up to 6; x has a value of 0 to 1, and y has a value of 5 to 6, dissolved in excess hydrogen fluoride. For this reason, the molar ratio of hydrogen fluoride to the addition compound should be not less than about 1:1 during the entire reaction. Advantageously, the molar ratio of hydrogen fluoride to addition compound is about 1:1 to 25:1, preferably about 3:1 to 10:1. In this case, the hydrogen fluoride addition compound is present in hydrogen fluoride in an amount of about 33 to 93% by weight, preferably about 60 to 81% by weight.

The ratio of hydrogen fluoride to hydrogen fluoride addition compound in the catalytically active solution can also be greater than 25:1. The catalytic activity of this solution is then smaller.

The reaction is preferably carried out without any trivalent antimony being present in the reaction mixture. It is also advantageous not to use any trivalent antimony when preparing the catalytically active solution.

An additional solvent, for example an inert halogenated hydrocarbon, is not required.

If desired, the process according to the invention can be carried out in the presence of additional reaction-promoting catalysts. The compound of formula (III) is preferably the only catalytically active component.

In order to prepare $CF_3CHCl_2$, the ethane or ethene derivative and, if desired, hydrogen fluoride are introduced into the previously prepared catalytically active solution in a preferred embodiment. The ethane or ethene derivative and the hydrogen fluoride can be introduced simultaneously, if desired as a mixture.

From the above description, it can be seen that hydrogen fluoride should always be present in the reaction mixture besides the addition compound and therefore not be consumed for the reaction with the starting compound(s). The amount of hydrogen fluoride used which exceeds the amount of hydrogen fluoride not participating in the reaction should be such that it corresponds at least to the amount necessary by stoichiometry for the chlorine/fluorine exchange or, if perchloroethylene is used as starting compound, for the hydrogen fluoride addition reaction and the chlorine/fluorine exchange. This amount preferably corresponds to a stoichiometric excess. Good results are obtained by using hydrogen fluoride in an amount which is 1.3 to 2.5 times the stoichiometrically required amount.

Optionally, hydrogen fluoride may be introduced at such a rate that a minimum ratio of free HF to addition compound of the formula (III) of about 1:1, for example 1:1 to 25:1, is always maintained in the reaction mixture.

It is advantageous to provide for thorough mixing of the catalytically active solution and the compound or mixture of compounds to be fluorinated, since a two-phase system may be formed. The advantageous thorough mixing can be achieved by suitable high-performance stirrers, by injection of a jet of inert gas, for example nitrogen, by injection of a jet of hydrogen fluoride, or by recirculating the reaction mixture by means of a pump via a static mixer.

The reaction can be carried out batchwise or continuously. In the batchwise procedure, the entire amount of ethane derivative and hydrogen fluoride is reacted in the presence of the catalytic solution in a reactor, and the reaction mixture obtained is then worked up. The work-up can be carried out, for example, by separating the volatile compounds by distillation, removing any entrained inorganic components by scrubbing, and then drying and condensing the reaction product. If desired, by-products which may be present can be separated from the desired product by further fractional separation, for example distillation.

The reaction is preferably carried out in a continuous procedure. This is done by feeding the compound to be fluorinated or the mixture of compounds to be fluorinated and hydrogen fluoride continuously into the reactor and simultaneously removing an amount of converted reaction mixture which corresponds to starting compounds fed in. In this process, hydrogen fluoride is introduced in such an amount that the minimum ratios of hydrogen fluoride to hydrogen fluoride addition compound of the formula (III) described above are maintained.

The reaction mixture removed from the reactor is separated, for example, by fractional distillation. Starting compounds contained in the reaction mixture remain in the higher-boiling fraction and can be recycled into the reactor. The volatile components can be worked up as described above.

Another possibility is to condense the reaction mixture driven out in the form of vapor. This leads to the formation of two phases. The heavier phase contains the desired fluorinated reaction product. This phase can be separated from the lighter phase and, if desired, worked up by distillation. The lighter phase contains hydrogen fluoride. This compound is advantageously recycled to the reactor. Uncondensed components of the reaction mixture, predominantly HCl, are passed through a gas scrubber filled with water. This removes the water-soluble components, in particular hydrochloric acid and any entrained hydrogen fluoride, from the gas. To remove any entrained organic components, the gas freed from HCl can be passed into a cold trap.

The reaction is advantageously carried out at temperatures of about 80° C. to 200° C., preferably 100° C. to 150° C. At lower temperatures, the reaction proceeds very slowly and requires long residence times. At higher temperatures, the formation of by-products increases.

The reaction is carried out at such a pressure that the reaction takes place in the liquid phase. The pressure is advantageously between 10 and 20 bar (abs.), preferably between 10 and 16 bar (abs.). Although it is also possible to work at higher pressures, this requires pressure devices which are correspondingly more expensive.

In a particularly preferred embodiment of the process according to the invention, the starting material is $CCl_2=CCl_2$. The reaction of $CCl_2=CCl_2$ with the hydrogen fluoride leads to the in situ formation of an intermediate which is a mixture containing $CFCl_2CHCl_2$. This mixture is directly reacted further to give $CF_3CHCl_2$.

Starting from $CCl_2=CCl_2$, the reaction is advantageously carried out in two steps. This particularly preferred embodiment of the process according to the invention is characterized in that the reaction of hydrogen fluoride with $CCl_2=CCl_2$ is carried out at a temperature of about 60° to 150° C., preferably 60° to 120° C., and a pressure of 10 to 30 bar (abs.), preferably 15 to 25 bar (abs.), with the in situ formation of mixtures containing $CFCl_2CHCl_2$, and the further reaction of the mixture containing $CFCl_2CHCl_2$ with further hydrogen fluoride at a temperature of about 80° to 200° C., preferably 100° to 150° C., and a pressure of 10 to 20 bar (abs.), preferably 10 to 16 bar (abs.).

Two particularly advantageous types of embodiment are available for carrying out this particularly preferred embodiment which uses a two-step procedure.

One type of embodiment is suitable in particular for the batchwise preparation of $CF_3CHCl_2$. Both steps are advantageously carried out in succession in the same reactor in this process. The subsequent procedure is such that the reaction of $CCl_2=CCl_2$ with hydrogen fluoride is first carried out under the conditions of the in situ preparation of the mixtures containing $CFCl_2CHCl_2$ with respect to temperature and pressure and, when a significant portion, i.e. for example more than 70% by weight of the $CCl_2=CCl_2$ which is initially present has been converted, the fluorination conditions with respect to temperature and pressure are established in the reactor.

The other type of embodiment is suitable for carrying out the process continuously. This type of embodiment is very particularly suitable for the industrial preparation of $CF_3CHCl_2$. In this embodiment, the in situ preparation of the mixtures containing $CFCl_2CHCl_2$ and their further reaction to give $CF_3CHCl_2$ is carried out spatially separated. Two reactors are used for this, using the catalytically active solution described above in both reactors. In this embodiment, too, it is advantageous to preferably introduce the reactants into the catalytically active solution.

In the first reactor, $CCl_2=CCl_2$ fed in continuously is reacted with hydrogen fluoride fed in continuously under a pressure and temperature suitable for forming $CFCl_2CHCl_2$ in situ. The resulting mixture containing $CFClC_2HCl_2$ is then passed into a second reactor and reacted there with hydrogen fluoride at a pressure and temperature suitable for forming $CF_3CHCl_2$. The reaction mixture is advantageously passed from the first to the second reactor in the vapor phase, since in this case at most small amounts of the catalytically active solution and small amounts of the starting compound(s) are entrained. Transfer can be effected, for example, by means of a backflow-proof pump.

The reaction product is a mixture containing hydrogen fluoride, hydrogen chloride, $CF_2ClCHCl_2$, $CF_3CHCl_2$ and impurities, for example $C_2Cl_3F_3$ and $C_2Cl_2F_4$. These and any further perhalogenated by-products are only formed in very small concentrations.

This product mixture can then, while releasing the pressure, be separated first by fractional condensation and then by workup through distillation.

If desired, the reaction mixture driven out of the second reactor can, before workup, be passed into a stabilizing zone. In this stabilizing zone, low boiling components of the organic phase, predominantly the desired reaction product, are separated as a gas. The condensed high boiling phase contains starting compounds and entrained catalyst products and is recycled into the reactor. For example, the stabilizing zone can comprise a stripper fitted with a distillation column. Here, the higher-boiling components of the reaction mixture are separated from the vapor stream by the distillation column and flow back into the reactor.

In this case, too, it is possible first to condense the reaction mixture driven out in the form of vapor. This then leads to the formation of two phases. The heavier phase containing the desired reaction product is separated from the lighter phase and can, if desired, additionally be worked up by distillation. The lighter phase contains hydrogen fluoride and is advantageously pumped back into the reactor(s).

Uncondensed components are again passed through a gas scrubber and, if desired, passed into a cold trap to separate any entrained organic components.

The 1,1,1-trifluoro-2,2-dichloroethane produced by this process can be used as an alternative to $CFCl_3$ as solvent or blowing agent. The partially fluorinated products, such as $CFCl_2CHCl_2$ and $CF_2ClCHCl_2$, can be recycled to the process of the invention. The inorganic fluorine-containing components, such as hydrogen fluoride, are also recycled. The hydrogen chloride which has been separated can be worked up to yield hydrochloric acid. If, in accordance with the preferred embodiment, the starting material in the process of the invention is $CCl_2=CCl_2$, it may be advantageous to recycle a portion of the hydrogen chloride which has been separated to the first reaction step, since this simple measure may contribute to increasing the reaction rate and the degree of conversion of the process of the invention.

A simple appropriate apparatus for carrying out the process according to the invention is shown in FIG. 1. Desired modifications of this apparatus can easily be made by one skilled in the art. For example, it is readily possible to provide a two-step reactor instead of the one-step reactor shown in FIG. 1.

The apparatus shown in FIG. 1 comprises a reactor R. This reactor R should advantageously be made of a material resistant to hydrogen fluoride and antimony halide. Examples of highly suitable reactors are those made of Hastelloy alloy. The reactor R has an inlet into which the starting materials can be introduced through line E. Further openings, not shown in the figure, allow temperature control and the removal of analytical samples. The reactor R furthermore has a stirrer operated by the motor M and an outlet for the reaction products. This outlet is connected to a distillation column D which, in turn, is connected to a reflux condenser RC. The reflux condenser RC is connected to a coolable condenser C via line G1. A pressure-maintaining valve PV1 is incorporated in line G1 between the reflux condenser RC and the condenser C.

The condenser C is connected to a phase separator PHS. In this phase separator PHS, a condensate consisting of two phases is formed. The heavier phase contains the organic reaction products. The lighter phase consists primarily of hydrogen fluoride. This upper phase is passed into an HF recycling tank RTHF and recycled into the reactor via a pump P through line F1.

The heavier phase is discharged through line F2 into a crude product tank CPT, from where it is, if desired, worked up by distillation.

Uncondensed gases descend via the gas line G2 and pressure-maintaining valve PV2 into a gas scrubber GS. Here, water-soluble components, particularly hydrochloric acid and any entrained hydrogen fluoride, are removed. The remaining gas leaving the gas scrubber is passed via line G3 into a cold trap CT. Here any entrained organic components are condensed.

Modifications of this apparatus can readily be made by one skilled in the art. Thus, for example, instead of the one-step reactor R a two-step reactor can be provided. If desired, the low-temperature condensation device can be connected to a further distillation column, these and further modifications of the apparatus used are considered to be within the skill of the art.

The process of the invention offers particular advantages:

it takes place in the liquid phase thereby saving energy;

the yield is many times higher than in previously known processes;

it can be operated continuously;

few by-products are formed, particularly few perhalogenated compounds;

the catalyst has a long life, and the waste disposal problems are correspondingly low.

The following examples are intended to illustrate the process of the invention in further detail without limiting its scope.

EXAMPLE 1

Batchwise Preparation of 1,1,1-Trifluoro-2,2-Dichloroethane

1.1 Apparatus Used

An autoclave having an interior volume of 30 liters was used as the reactor. The autoclave was equipped with a stirrer and a closable inlet for introducing the starting compounds. It was equipped via an outlet with a fitted distillation column and a reflux condenser attached to the column.

The reflux condenser was connected to a gas line leading into a coolable condenser. The condenser was connected to a phase separator via a line. A gas line extended from the phase separator into a gas scrubber. The gas scrubber was connected to a low-temperature condenser. A pressure-maintaining valve incorporated in the gas line behind the reflux condenser kept the pressure in the autoclave constant.

The phase separator was furthermore connected to a crude product tank, into which the heavier organic phase could be discharged, and to a tank into which the lighter phase containing hydrogen fluoride could be discharged.

The distillation column and the reflux condenser were temperature-controlled at 90° C. during the reaction. Here, unconverted organic components were condensed and recycled to the reactor.

1.2. Preparation of the Catalytically Active Solution 11.0 kg (550 moles) of hydrogen fluoride were initially introduced into the autoclave, and 26.3 kg (121.5 moles) of antimony pentafluoride were added with stirring. A solution of $H_2F^+(SbF_6)^-$ in hydrogen fluoride was formed.

1.3. Fluorination of Perchloroethylene to Give Trifluoro-2,2-Dichloroethane 2.7 kg (135 moles) of hydrogen fluoride and 5.84 kg (35 moles) of perchloroethylene were added to the catalytically active solution described under 1.2. The reaction mixture was stirred at 135° C. for 8 hours. During the reaction, gases evolved, primarily hydrogen chloride, which led to an increase in pressure. The pressure was controlled at a maximum pressure of about 16 bar (abs.) by appropriate adjustment of the pressure-maintaining valve located behind the cooler. As soon as the pressure in the reaction system exceeded the set maximum pressure, gaseous reaction products, particularly HCl, were discharged from the autoclave behind the distillation column and the reflux condenser via the pressure-maintaining valve. High-boiling components were condensed at the same time in the distillation column and the reflux condenser and recycled to the autoclave. The gases escaping via the pressure-maintaining valve, particularly hydrogen chloride, were removed in the gas scrubber which contained water as the absorbent.

After the evolution of gas had ceased, the reaction mixture was cooled to about 90° to 100° C., and the distillation column, the reflux condenser and the water in the gas scrubber were temperature-controlled at about 50° C. The pressure-maintaining valve was opened, thus allowing the autoclave pressure to drop to ambient pressure. Under ambient pressure, the reaction product is gaseous at the conditions mentioned. The gaseous reaction product escaping from the autoclave was passed through the coolable condenser. Condensable products were liquefied and collected in the phase separator. Gaseous products, containing in particular HCl, were passed into a gas scrubber.

4.86 kg of an organic reaction product were discharged from the phase separator into the crude product tank. The reaction product was analyzed by gas chromatography. It comprised about 97.3% by weight of 1,1,1-trifluoro-2,2-dichloroethane in addition to small amounts of 1,1-difluoro-1,2,2-trichloroethane and 1,1,1,2-tetrafluoro-2,2-dichloroethane. The yield was 87%, relative to the perchloroethylene used. The product was further purified by distillation.

EXAMPLE 2

Continuous Preparation of 1,1,1-Trifluoro-2,2-Dichloroethane

2.1. Apparatus Used

The apparatus used in this example corresponded to the apparatus described in Example 1.1., and a 5 liter pressure reactor made of Hastelloy[198] C22 (a nickel alloy resistant to hydrogen fluoride) and fitted with separation column and cooler was used this time as the reactor. This time the separation column and the cooler were temperature-controlled at 85° C.

2.2. Preparation of the Catalytically Active Solution 5 kg (23.4 mole) of antimony pentafluoride were dissolved in 1.7 kg of hydrogen fluoride in the pressure reactor with stirring.

2.3. Reaction Procedure

A mixture of perchloroethylene and hydrogen fluoride was introduced continuously into the reactor temperature-controlled at about 125° to 130° C. During the reaction, gases evolved which led to an increase in pressure. The pressure-maintaining valve was set in such a manner that the maximum pressure was 16 bar (abs.). 2,270 g of perchloroethylene and 1,500 g of hydrogen fluoride were metered in over a period of 7 hours.

The gases leaving the reaction system were condensed and collected in the phase separator to give 2,134 g of crude product. The crude product contained 75.9% by weight of 1,1,1-trifluoro-2,2-dichloroethane, 21.8% by weight of 1,1-difluoro-1,2,2-trichloroethane, furthermore 1.1% by weight of perchloroethylene and 1.2% by weight of perhalogenated product. The mixture was worked up by distillation, it being possible for the 1,1-difluoro-1,2,2-trichloroethane portion to be recycled into the reactor for further reaction.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for preparing ethane derivatives of the general formula (I)

$$CF_3CHYZ \qquad (I)$$

in which Y and Z may be the same or different and Y is hydrogen, fluorine, chlorine or bromine and Z is hydrogen, fluorine, chlorine or bromine, comprising:

reacting at least one ethane derivative corresponding to the formula II:

$$CHal^1Hal^2Hal^3CHYZ \qquad (II)$$

in which Y and Z have the above meanings, $Hal^1$ is halogen, $Hal^2$ is halogen and $Hal^3$ is halogen with the exception of fluorine with essentially anhydrous hydrogen fluoride in liquid phase in the presence of an essentially anhydrous, catalytically active solution of a hydrogen fluoride addition compound corresponding to the formula III:

$$H_2F^+(SbCl_xF_y)^- \qquad (III)$$

in which x plus y=6, and x has an average value from 0 to 0.5 and y has an average value from 5.5 to 6, in hydrogen fluoride, and recovering the resulting ethane derivative of formula (I) from the reaction mixture.

2. A process according to claim 1, wherein the starting ethane derivative is a mixture containing a compound corresponding to the formula IIa:

$$CFHal^2Hal^3CHYZ \qquad (IIa)$$

in which $Hal^2$, $Hal^3$, Y and Z have the above meanings, said mixture being prepared in situ by reacting an ethene compound corresponding to the formula IV:

$$CHal^2Hal^3=CYZ \qquad (IV)$$

in which $Hal^2$, $Hal^3$, Y and Z have the above meanings, with essentially anhydrous hydrogen fluoride in liquid phase in the presence of the catalytically active solution.

3. A process according to claim 1, wherein Y and Z represent chlorine.

4. A process according to claim 1, wherein $Hal^3$ is chlorine, and $Hal^1$ and $Hal^2$ are fluorine or chlorine.

5. A process according to claim 1, wherein a compound of formula II selected from the group consisting of $CCl_3CHCl_2$, $CFCl_2CHCl_2$, $CF_2ClCHCl_2$ and mixtures thereof, is reacted to form $CF_3CHCl_2$, and the resulting $CF_3CHCl_2$ is recovered from the reaction mixture.

6. A process according to claim 1, wherein the molar ratio of hydrogen fluoride to hydrogen fluoride addition compound in the reaction mixture is at least 1:1.

7. A process according to claim wherein said reaction is carried out at a temperature in the range from 80° C. to 200° C. and a pressure in the range from 10 to 20 bar (abs.).

8. A process according to claim 7, wherein said reaction is carried out at a temperature in the range from 100° C. to 150° C. and a pressure in the range from 10 to 16 bar (abs.).

9. A process according to claim 5, wherein said compound of formula II is a $CFCl_2CHCl_2$-containing mixture produced in situ by reacting $CCl_2=CCl_2$ with essentially anhydrous hydrogen fluoride in liquid phase in the presence of the catalytically active solution.

10. A process according to claim 9, wherein the in situ reaction of $CCl_2=CCl_2$ to produce the $CFCl_2CHCl_2$-containing mixture is carried out at a temperature in the range from about 60° C. to 50° C. and a pressure in the range from 10 to 30 bar (abs.), and the further reaction of the $CFCl_2CHCl_2$-containing mixture is carried out at a temperature in the range from 80° to 200° C. and a pressure in the range from about 10 to 20 bar (abs.).

11. A process according to claim 10, wherein the in situ reaction of $CCl_2=CCl_2$ to produce the $CFCl_2CHCl_2$-containing mixture is carried out at a temperature in the range from 60° C. to 120° C. and a pressure in the range from 15 to 25 bar (abs.), and the further reaction of the $CFCl_2CHCl_2$-containing mixture is carried out at a temperature in the range from 100° to 150° C. and a pressure in the range from 10 to 16 bar (abs.).

12. A process according to claim 1, wherein said catalytically active solution is produced by reacting an antimony compound corresponding to the formula $SbCl_nF_{5-n}$, in which $n=0$ to 5, with an amount of hydrogen fluoride sufficient to form a solution of the compound of formula III in hydrogen fluoride at such a temperature and such a pressure that the $SbCl_nF_{5-n}$ is substantially completely reacted to form $H_2F^+(SbCl_xF_y)^-$, in which x and y have the meanings given above.

13. A process according to claim 12, wherein antimony pentafluoride is reacted with hydrogen fluoride.

14. A process according to claim 12, wherein said catalytically active solution is prepared by reacting antimony pentachloride and hydrogen fluoride at a temperature in the range from about 20° C. to 100° C. and at a pressure in the range from about 0.5 to 8 bar (abs.).

15. A process according to claim 1, wherein x represents 0 and y represents 6.

* * * * *